(12) United States Patent
Lu et al.

(10) Patent No.: US 8,491,894 B2
(45) Date of Patent: Jul. 23, 2013

(54) **METHOD FOR INHIBITING THE GROWTH OF *MYCOBACTERIUM TUBERCULOSIS* BY USING CD13 RECEPTOR**

(75) Inventors: Yen-Ta Lu, Taipei (TW); I-Fang Tsai, Taipei (TW)

(73) Assignee: Mackay Memorial Hospital, Taipei (TW)

( * ) Notice: Subject to any disclaimer, the term of this patent is extended or adjusted under 35 U.S.C. 154(b) by 29 days.

(21) Appl. No.: 13/164,137

(22) Filed: Jun. 20, 2011

(65) Prior Publication Data

US 2012/0064624 A1 Mar. 15, 2012

(30) Foreign Application Priority Data

Sep. 14, 2010 (TW) ................................. 99131076 A

(51) Int. Cl.
*A61K 39/395* (2006.01)
*A61K 39/04* (2006.01)
*A61K 39/00* (2006.01)

(52) U.S. Cl.
USPC .................. 424/130.1; 424/164.1; 424/184.1; 424/234.1; 424/248.1

(58) Field of Classification Search
USPC ........... 424/130.1, 164.1, 184.1, 234.1, 248.1
See application file for complete search history.

*Primary Examiner* — Rodney P. Swartz
(74) *Attorney, Agent, or Firm* — WPAT, P.C.; Anthony King

(57) ABSTRACT

The present invention discloses a method for inhibiting the growth of *Mycobacterium tuberculosis*, comprising: administering at least one selective binding agent such as an anti-CD13 antibody or a CD13 antagonist which can bind a CD13 receptor of a cell to inhibit infection of *Mycobacterium tuberculosis*. Administration of anti-CD13 antibody can reduce an expression level of the CD13 receptor, inhibit entry of *Mycobacterium tuberculosis* into monocytes, reduce survival of *Mycobacterium tuberculosis* in monocytes, and kill *Mycobacterium tuberculosis* effectively.

6 Claims, 10 Drawing Sheets

(4 of 10 Drawing Sheet(s) Filed in Color)

METHOD FOR INHIBITING THE GROWTH OF *MYCOBACTERIUM TUBERCULOSIS* BY USING CD13 RECEPTOR

CROSS-REFERENCE TO RELATED APPLICATION

The present application claims priority to Taiwan Patent Application Serial Number 099131076 filed on Sep. 14, 2010, the disclosure of which is incorporated herein by reference in its entirety.

BACKGROUND OF THE INVENTION

1. Field of the Invention

The present invention is related to an application of cell surface receptor that binds *Mycobacterium tuberculosis*, especially relating to an application of CD 13 receptor on inhibition of *Mycobacterium tuberculosis* infection of monocytes.

2. The Prior Arts

Tuberculosis (TB), with estimated annual death of two million cases, is a common deadly transmissible disease in developing countries. According to the World Health Organization's report, the average annual increase in tuberculosis is about 2% in recent years. The pathogen of TB is called *Mycobacterium tuberculosis* complex (MTBC), including *Mycobacterium tuberculosis, M. bovis, M. africanum, M. microti*, and *M. canetti*, in which *Mycobacterium tuberculosis* is the main pathogen of TB in human and the main infection site is lung.

It is estimated that one third of world populations (about 1.7 million/year) are infected with *Mycobacterium tuberculosis*. This is because virulence factor of *Mycobacterium tuberculosis* can enable the bacterium to avoid being killed by phagocytes and survive within host phagocytes. In the aspect of phagocyte detection of *Mycobacterium tuberculosis*, many receptors on the surface of *Mycobacterium tuberculosis* are important, indicating that receptors that facilitate mycobacterial entry into phagocytes have impact on survival opportunity of *Mycobacterium tuberculosis*. *Mycobacterium tuberculosis* binds to the cholesterol of phagocytes and lipid-rich region (also called lipid rafts) of host cell membrane, a site also having function of signal transduction. Inside host cells, *Mycobacterium tuberculosis* can degrade cholesterol as energy source during persistence of chronic infection. In addition, *Mycobacterium tuberculosis* will affect lipid transduction to block phagosome synthesis so as to protect itself from being transported to lysosome.

CD13 (aminopeptidase N) is a multi-functional protein present in many tissues that not only functions as an enzyme but reveals other functional activities through different mechanisms. CD 13 is found partly distributed in lipid rafts and affects cell membrane protein composition and cholesterol uptake. CD13 has been found in membrane-bound protein and in secretion of specific cells and degraded cell membrane in active form. For some specific virus, CD13 is a cell surface receptor, where virus can enter into cells by endocytosis.

SUMMARY OF THE INVENTION

However, it is not clear how *Mycobacterium tuberculosis* interacts with cell surface receptors, through which surface receptor it enters and infects cells, or by what kind of mechanism to survive in cells. Furthermore, no solution on inhibition of *Mycobacterium tuberculosis* has been developed regarding combined issues described above.

Therefore, a primary object of the present invention is to provide a method for inhibiting the growth of *Mycobacterium tuberculosis*, comprising: administering at least one selective binding agent binding to a CD13 receptor to prevent a cell from infection by *Mycobacterium tuberculosis*, wherein the selective binding agent is an anti-CD13 antibody or a CD13 antagonist, and the anti-CD13 antibody is WM15 antibody or WM47 antibody, to reduce an expression level of the CD13 receptor, to reduce endocytic internalization of *Mycobacterium tuberculosis* which results in entry into the cell and to reduce survival of *Mycobacterium tuberculosis* in the cells.

The present invention demonstrate that not only a CD13 receptor of monocytes is a novel receptor to *Mycobacterium tuberculosis*, but also the CD13 receptor can promote endocytic internalization of *Mycobacterium tuberculosis* which results in entry into human monocytes. Therefore, administration of the selective binding agent such as anti-CD13 antibody can reduce the expression level of the CD13 receptor, inhibit entry of *Mycobacterium tuberculosis* into monocytes, decrease survival of *Mycobacterium tuberculosis* in cells, and kill *Mycobacterium tuberculosis* effectively.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE PREFERRED EMBODIMENT

Definition

Figure 1:
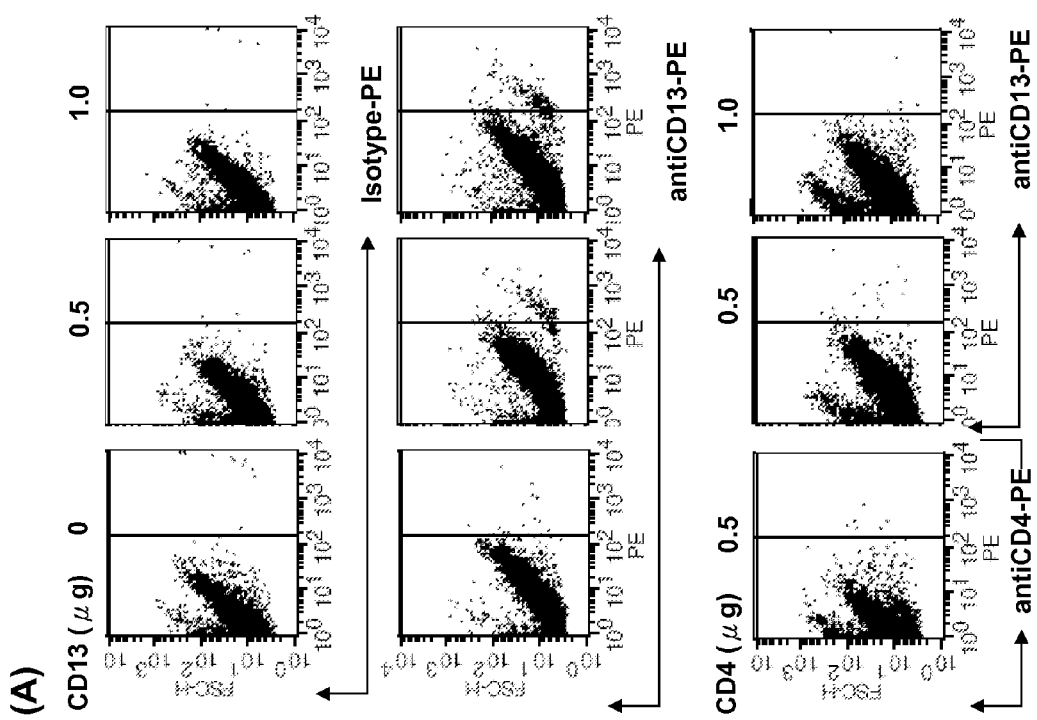
FIGS. 1A~1E show interaction diagram of CD13 protein and *Mycobacterium tuberculosis*: (A) *Mycobacterium tuberculosis* cultivated with or without CD13 receptor protein, and stained with PE-conjugated anti-CD13 antibody and an isotype antibody as negative control. An irrelevant protein CD4 was used, to assess whether the binding of *Mycobacterium tuberculosis* were specific for CD13. No apparent binding was observed between CD4 (0.5 µg) and *Mycobacterium tuberculosis* (FIG. 1A, bottom row). (B) As shown by flow cytometry, dose-dependent increases of CD13-positive *Mycobacterium tuberculosis* organisms were found and the binding of CD13 to *Mycobacterium tuberculosis* may up to 6.53±0.01%. (C) *Mycobacterium tuberculosis* cultivated with MNPs or CD13-MNPs. An external magnetic field was applied. Precipitate of MNPs was dark black color, and CD 13-MNPs precipitate was light color, indicating the latter overlay part of the original color. (D) In the aspect of concentration of *Mycobacterium tuberculosis* in the suspension, bacterial number in CD13-MNPs treated group was significantly lower than that of MNPs group. (E) Results of acid-fast stain of untreated MNPs aggregates showed scattered stained bacterium, as compared with large CD13-MNPs aggregates surrounded by many stained bacterium.
Figure 1:
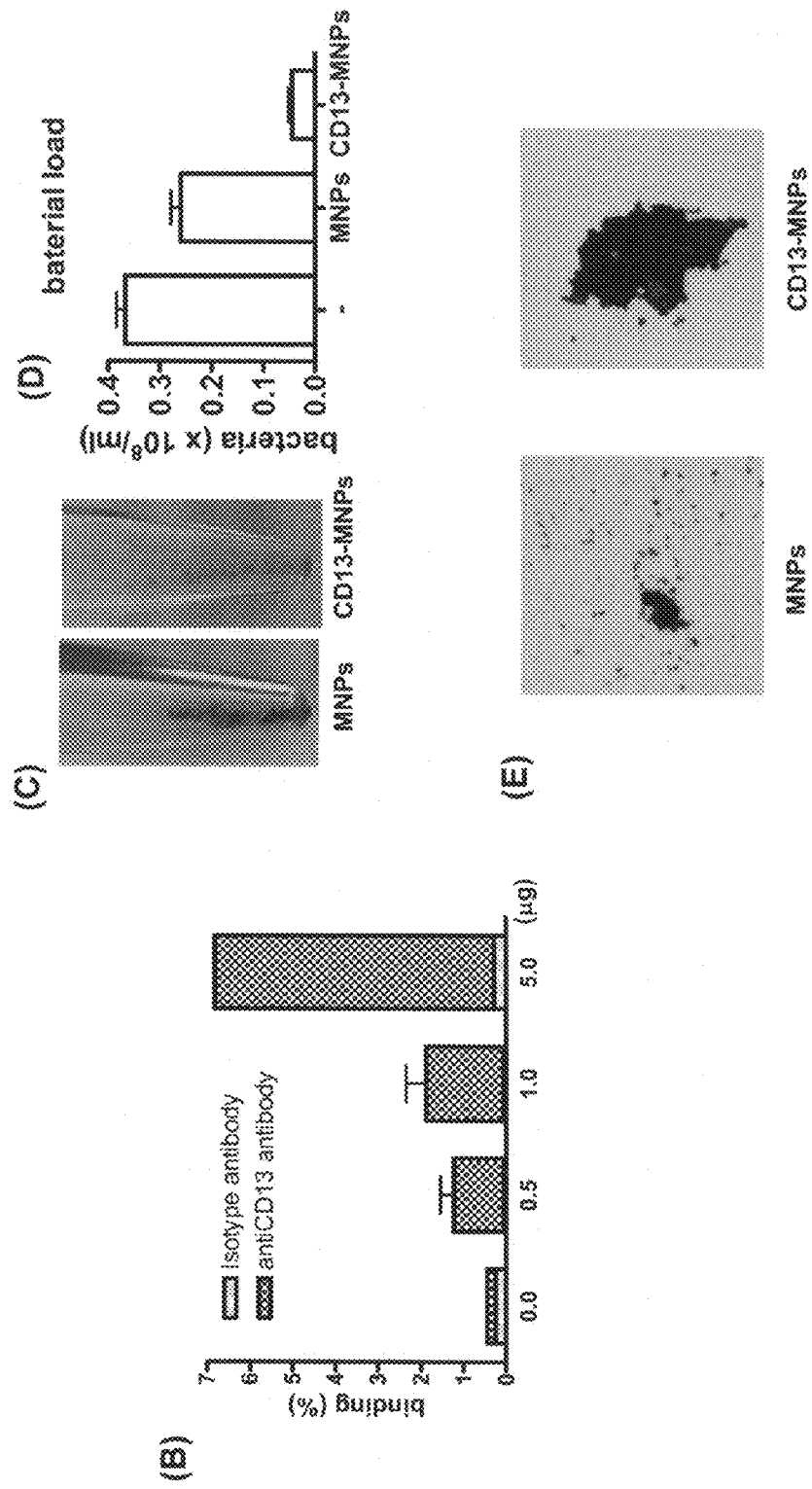

The term of "Monocyte" is also called monocuclear white cell, belongs to a type of white blood cells involved in first-line defensive mechanism and is recognized to be able to differentiate into a dendritic cell or macrophage precursor. Monocytes normally move in the blood system. In response to external stimulating signals, monocytes secrete many immuno-regulatory cytokines, move to the site of infection in the tissues and differentiate into pacrophages.

The term of "*Mycobacterium tuberculosis*" is a Gram-positive, aerobic bacteria that causes tuberculosis in human, primate animals and animals. One third of the global population is infected with *Mycobacterium tuberculosis*; therefore, tuberculosis is still the most important infectious disease today.

The term of "CD13 receptor" is one of the receptors that is distributed on cell surface. It has important biological functions, such as promotion of cell differentiation, involvement in angiogenesis and immune response, and function as a cell surface receptor.

The term of "epitope" is the site recognized or bound by antibody is called antigenic determinant or epitope, which can be a three dimension conformation structure or two dimension sequence determinant. Normally an antigen has many epitopes. The more complex of structure or the bigger of an antigen molecule, the more numbers of epitopes can be found on an antigen.

Materials and Methods

Source of materials used in the embodiments are shown below: Cholesterol and Trypan blue were purchased from Sigma-Aldrich Co. (MO, USA); RPMI-1640 medium and PBS were purchased from GIBCO (Invitrogen, Grand land, NY, USA); FBS was purchased from Biological Industries (Haemek, Israel); L-J medium slant and 7H11 agar were purchased from Creative Media Products, Ltd (Taipei, Taiwan); TB Auramine-Rhodamine T was purchased from Becton, Dickinson and Company (Maryland, USA); Ficoll-Paque PLUS (cell density gradient separation solution) was purchased from Amersham Biosciences (AB, Uppsala, Sweden); CD14 microbead was purchased from Miltenyi Biotec GmbH (Bergisch Gladbach, Germany); Antibodies against CD13 without sodium azide for cell-treatment were purchased: clone WM15 from Biolegend, clone WM47 from Santa Cruz Biotechnology, and isotype (mouse IgG1κ) from Biolegend; Mouse anti-CD13 antibody (clone WM47), anti-Rab5 (clone Rab5-65) antibody, and anti-Rab7 (clone Rab7-117) antibody were purchased from ABcam (Cambridge, UK); PE-conjugated mouse antibody against isotype (IgG1κ) or CD13 (clone L138) or CD4 (clone RPA-T4) were purchased from BD Pharmingen; Anti-*Mycobacterium tubercu*-

*losis* antibody was purchased from Biodesign International (Meridian Life Science Inc., Saco, Me.); PE-conjugated anti-mouse IgG was purchased from Jackson Immuno Research Laboratories Inc (PA, USA); recombinant human CD13 protein (residues 69-967) was purchased from R& D Systems, Inc. (Minneapolis, Minn., USA) and CD4 (residues 26-226) was purchased from abcam; Lab-Tek Chamber Slides (cell culture slides) was purchased from Nalge Nunc International (NY, USA); and BD Cytoperm Permeabilization buffer was purchased from BD Biosciences (San Jose, Calif., USA); DCFDA (2'-7'-dichloro-fluorescin diacetate and LysoSensor Yellow/Blue dextran were purchased from Molecular Probes.
Preparation of Viable *Mycobacterium tuberculosis* (MTB)

*Mycobacterium tuberculosis* used in the present invention was culture collection of the Mycobacteriology Laboratory and cultured by MacKay Memorial Hospital in Taiwan. *Mycobacterium tuberculosis* was cultivated on L-J slant medium at 37° C. and 10% $CO_2$. At mid log phase, *Mycobacterium tuberculosis* was harvested and resuspended in PBS. Cell suspension's turbidity was adjusted to 0.5 McFarland units (about $1\times10^8$ cells/ml).

Cell and Cell Cultivation

Peripheral blood mononuclear cells (PMBC) were isolated from whole blood by Ficoll-Paque density gradient centrifugation and cultivated on CD14 microbeads. CD14 positive monocytes were isolated by magnets. Cells were cultivated in RPMI-1640 medium in a U-bottom 96 well plate at cell density of $2\times10^5$ cells/2001 with or without supplementation of isotype antibody or CD13 monoclonal antibody (WM15 or WM47) for 1 hr, followed by adding *Mycobacterium tuberculosis* (concentration at $5\times10^5$ cells) to each well and cultivated for another 24 hrs. Cell survival was determined by Trypan blue staining method.

Flow Cytometric Assay

For cell staining, PE-conjugated anti-CD13 antibody (clone WM15) was used to stain cell surface. Cells were perforated with permeabilization buffer, amount of intraceullular Rab5 and Rab7 were determined using Rab5 antibody and Rab7 antibody as a primary antibody and PE-conjugated anti-mouse IgG as a secondary antibody. FACS Calibur flow cytometer (BD Bioscience) was used to trap stained cells and the results were analyzed using CellQuest software (BD Bioscience).

Nile Red Staining

A stock solution of nile red (1 mg/ml) in acetone was prepared and stored at 4° C. and protected from light. The nile red solution was added to the cell preparation (final concentration: 1 μg/ml) for 10 minutes and excess dye was washed away with PBS. Nile red fluorescence was examined at two spectral settings, yellow-gold fluorescence (FL1 channel, excitation, 488 nm; emission, 530±30 nm) for cytoplasmic neutral lipids and red fluorescence (FL2 channel, excitation, 488 nm; emission, 585±21 nm) for polar lipids, consist of phospholipids, other amphipathic lipids, and strongly hydrophobic proteins of cell membranes as reported. Stained cells were evaluated by flow cytometer and confocal laser scanning microscopy.

Interaction between CD13 protein and *Mycobacterium tuberculosis* Binding of soluble CD13 protein to viable *Mycobacterium tuberculosis* was determined using flow cytometry. Cell suspension (about $1\times10^7$ cells/ml) was incubated with 0.5 μg recombinant CD13 protein (residue 69-967) or CD4 (residues 26-226) at 37° C. for 30 minutes. Then cells were washed with PBS twice and centrifuged at 3,500 g at 4° C. for 15 minutes. Precipates were resuspended in PBS, supplemented with CD13 antibody (clone L138) or isotype antibody (IgG K) or CD4 antibody (clone RPA-T4), allowed to react for 30 min, washed with PBS twice and centrifuged at 3,500 g at 4° C. for 15 minutes. Before flow cytometer analysis, precipitates in PBS solution were mixed with equal volume of 4% formalin and allowed to react for 24 hrs. The magnetic nanoparticles (MNPs), triferric tetraoxide magnetic beads coated with nitrilotriacetic acid derivative (NTA), used in the present invention were provided by Dr. Yu-Chie Chen (National Chiao Tung University). Recombinant His-tagged CD13 protein was immobilized on the NTA-MNPs surface through Ni. Binding of *Mycobacterium tuberculosis* ($10^8$ cells/ml, 200 μl) to MNPs or CD13-MNPS was determined by mixing *Mycobacterium tuberculosis* with MNPs or CD13-MNPs then followed by observation of precipitate formation. External magnetic field was applied to remove *Mycobacterium tuberculosis* or CD13-MNPs precipitates, and non-binding *Mycobacterium tuberculosis* was measured by spectrophotometer at 600 nm.

Binding of CD13 protein on the monocyte membrane to the *Mycobacterium tuberculosis* was measured by confocal microscope. Monocytes (about $2\times10^5$ cells) were incubated in 8 well slide and were infected with Auramine-Rhodamine T labeled *Mycobacterium tuberculosis*. After 30 minutes infection, non-binding bacteria were washed off with PBS and remained cells were fixed with 4% formalin. CD13 protein was stained with FITC conjugated anti-CD13 antibody, and nucleus was stained with 4'-6-Diamidino-2-phenylindole (DAPI). To study binding connection between CD13 protein and *Mycobacterium tuberculosis*, confocal microscope (Leica TCS SP5, Wetzlar, Germany) was used to analyze monocytes infected by Auramine-Rhodamine T labeled *Mycobacterium tuberculosis*.

CD13 Protein Mediated Internalization of *Mycobacterium tuberculosis*

CD13-dependent internalization of *Mycobacterium tuberculosis* was detected by flow cytometry. Monocytes (about $2\times10^5$ cells) were treated with isotype or WM15 or WM47 antibody for 1 hr and then cultivated with *Mycobacterium tuberculosis* (cell density: $5\times10^5$ cells) for 24 hrs. Non-binding *Mycobacterium tuberculosis* were washed off with PBS and the remained cells were fixed with 4% formalin at 4° C. for 24 hr. Perforation of mycobacterial cells were done using permeabilization buffer, and stained with FITC-conjugated anti-MTB antibody for 1 hr. After washing, 0.1% trypan blue was added and the solution was placed on ice for 2 mins to inhibit extracellular fluorescencent residual. The percentage of intracellular *M. tuberculosis* was measured relative to the isotype control (100%) by flow cytometry.

Survival of Intracellular *Mycobacterium tuberculosis*

Monocytes ($2\times10^5$ cells) were cultivated in a U-bottom 96 well plate. Cells were pre-treated with WM15 or WM47 for 1 hr and incubated with *Mycobacterium tuberculosis* ($5\times10^5$ cells). At 24 hr and 72 hr, monocytes were collected and washed with PBS three times. A part of the cell suspension was stained with trypan blue to determine survival ratio and cell count. The other part of the cell suspension was added in 100 μl 0.1% SDS solution to lyse the cells, followed by shaking for 10 minutes and centrifugation. After centrifugation, 900 μl water was added to resuspend the pellet, and shook for 10 minutes then centrifuged at 3,400 g for 15 minutes. 50 μl of cell lysate in PBS was inoculated into Lowenstein-Jensen medium or 7H11 agar, and the lysate were washed with PBS twice. Inoculated plate was incubated at 37° C. for 3 weeks at controlled $CO_2$ (10%) level. The results were shown in average Colony Forming Unit (CFU) formed per 10,000 monocytes. To prove that growth of *Mycobacterium tuberculosis* was regulated by WM15 and WM47, monocytes incubated with *Mycobacterium tuberculosis*

($5\times10^5$ cells) for 24 hrs were post-treated with WM15 and WM47 for another 24 hrs. Survival ratio of *Mycobacterium tuberculosis* inside monocyte was tested as described before, and the results were expressed as average CFU/10,000 monocytes.

Confocal Microscopy

For pH measurement, monocytes were incubated with 1 mg/ml LysoSensor Yellow/Blue dextran (Molecular Probes) for 16 hours and then washed with PBS. To performed pH titration as standard, monocytes incubated with LysoSensor Yellow/Blue dextran overnight and replaced the medium with titrated pH reaction buffer consisting of 5 mM NaCl, 115 mM KCl, 1.2 mM MgSO4, 25 mM 4-morpholineethanesulfonic acid, followed by monesin (10 μM) and nigericin (20 μM) treatment. The treated cells were equilibrated for 10 min with the pH reaction buffer titrated between pH 4.5 and 6.5. After incubation, the labeled cells were observed with Olympus IX71 inverted microscope and the 520/420 nm emission was calculated for endocytic vesicles by MetaMorph Image software. Around 250 vesicles of five low-power fields per conditions were counted and the mean pH value of monocytes with isotype, WM15 and WM47 treatment was determined by comparing with known pH standards. As pH value was associated with the stage of phagosomal maturation, the number of vesicles with pH<4.8 (active lysosomes) and pH>4.8 (inactive lysosomes) was counted and the percentage of active lysosomes was represented.

Supernants Levels of TNF-α and IL-6

TNF-α and IL-6 supernatants were measured by ELISA kits (Biosource), in accordance with the manufacture's instructions.

Statistical Analysis

Paired t test was used for analysis. Data are reported as the mean±SEM. All statistical analysis was performed using Prism 3.0 software (GraphPad Software Inc., San Diego, Calif.). Two-sided tests were also used, and P<0.05 meant statistical significance.

EXAMPLE 1

Interaction Between CD13 Protein and *Mycobacterium tuberculosis*

To determine if *Mycobacterium tuberculosis* reacted with CD13 protein, viable *Mycobacterium tuberculosis* was cultivated with or without recombinant human CD13 protein for 30 minutes, and binding of CD13 protein to *Mycobacterium tuberculosis* was detected using PE-conjugated anti-CD13 antibody staining, and an isotype antibody as negative control. An irrelevant protein CD4 was used, to assess whether the binding of *Mycobacterium tuberculosis* was specific for CD13. No apparent binding was observed between CD4 (0.5 μg) and *Mycobacterium tuberculosis*. Materials, methods and detailed processes were the same as described above, and results are shown in FIGS. 1A-1E.

As shown by flow cytometry, dose-dependent increases of CD13-positive *Mycobacterium tuberculosis* organisms were found and the binding of CD13 to *Mycobacterium tuberculosis* reaches up to 6.53-0.01% (FIGS. 1A-1B).

To further evaluate binding effect, magnetic nano-particles labeled with (CD13-MNPs) were used as a tracing tool to evaluate binding affinity between *Mycobacterium tuberculosis* and CD13 protein. An external magnetic field was applied to accelerate aggregate formation. FIG. 1B showed comparison of precipitate colors. Compared with the brown precipitate of MTB-MNPs in MNPs treated group, the precipitate of MTB-CD13 MNPs in the CD13 MNPs treated group showed lighter color. The results suggested that large amount of *Mycobacterium tuberculosis* binding to CD13-MNPs could mask brown precipitate of MTB-CD13 MNPs.

To calculate the amount of bound *Mycobacterium tuberculosis* in the solution, mycobacterial density was measured at 600 nm after removal of precipitates. As shown in FIG. 1C, density of *Mycobacterium tuberculosis* was $0.37\pm0.02\times10^8$/ml before addition of nano-particles. Ten minutes after addition of nano-particles, less amount of *Mycobacterium tuberculosis* ($0.04\pm0.01\times10^8$/ml) was detected in MTB-CD13 MNPs group when compared with MTB-MNPs group ($0.26\pm0.02\times10^8$/ml).

After acid-fast stain, most of the MNPs could not bind to *Mycobacterium tuberculosis* and dispersed in observation zone. On the contrary, CD13-MNPs binding to *Mycobacterium tuberculosis* formed aggregates that could be observed under microscope. These results indicated that soluble CD13 protein could bind to *Mycobacterium tuberculosis*.

To further evaluate if CD13 protein interacted with *Mycobacterium tuberculosis* on the surface of monocytes, viable *Mycobacterium tuberculosis* were cultivated with monocytes for 30 minutes and then observed by confocal microscope. As shown in FIG. 2A, *Mycobacterium tuberculosis* attached to the surface of monocyte at the site where CD13 protein located. *Mycobacterium tuberculosis* was found attached to the surface of the monocytes with a 13.1±4.7% co-localization rate. Therefore, both soluble and surface bound CD13 protein could bind to *Mycobacterium tuberculosis* and might play a role as a receptor for *Mycobacterium tuberculosis* to bind on monocyte surface.

EXAMPLE 2

Internalization of *Mycobacterium tuberculosis* via Monocyte

Figure 2:
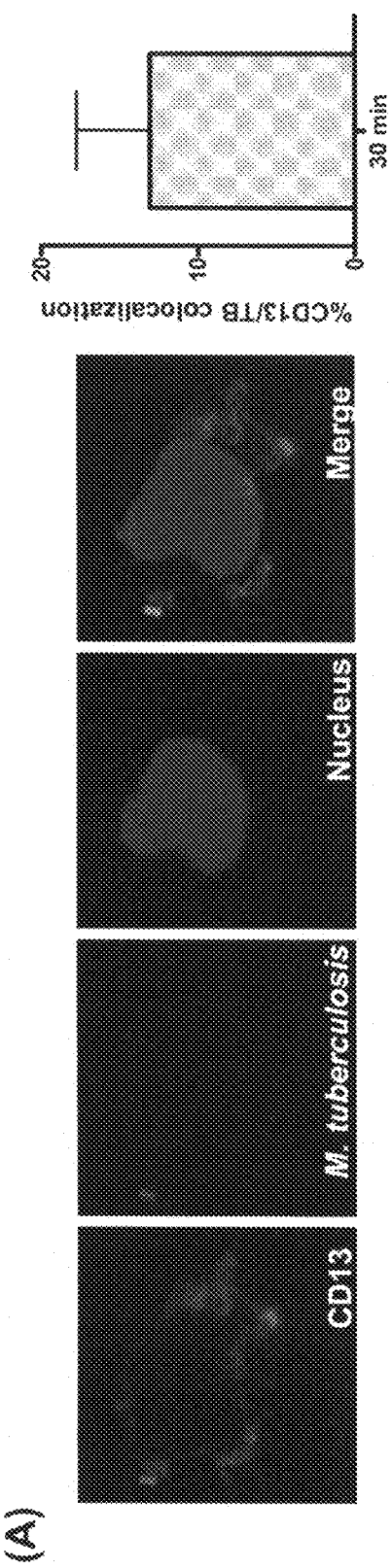
FIGS. 2A-2C show internalization of *Mycobacterium tuberculosis* in monocytes. (A) Confocal microscope photo of surface CD13 protein of monocyte stained with anti-CD13 antibody (green), *Mycobacterium tuberculosis* stained with TB Auramine-Rhodamine T (red), and nucleus stained with DAPI (blue), and a merge photo showing the site of CD13 protein on monocyte surface super-imposed with the site of *Mycobacterium tuberculosis* binding on monocytes. Each panel showed a representative cell. Bacteria that attached to the cells and merged with CD13 as yellow color were scored as colocalized with CD13 and a minimum of 100 bacteria were scored at 30 minutes. *Mycobacterium tuberculosis* was found attached to the surface of the monocytes with a 13.1±4.7% co-localization rate. (B) Monocytes were treated with isotype antibody (10 μg/ml) or WM15 antibody (10 μg/ml) or WM47 antibody (10 μg/ml) for 24 hrs. The expression level of CD13 protein was determined by PE-conjugated anti-CD13 antibody using flow cytometry, and the results of CD13-positive percentage were 97.6±0.7%, 7.2±6.0% and 17.1±8.7%, respectively. WM15 antibody or WM47 antibody blocked CD13 protein. (C) The percentage of intracellular *Mycobacterium tuberculosis* was measured by flow cytometry and data were expressed as percentages of intracellular MTB relative to control values (100%, isotype antibody) and seven independent experiments were shown. As compared with isotype control, treatment with WM15 (10 μg/ml) and WM47 (10 μg/ml) reduced *Mycobacterium tuberculosis*-positive monocytes to 81.6±7.1% and 73.2±6.0%, respectively.
Figure 2:
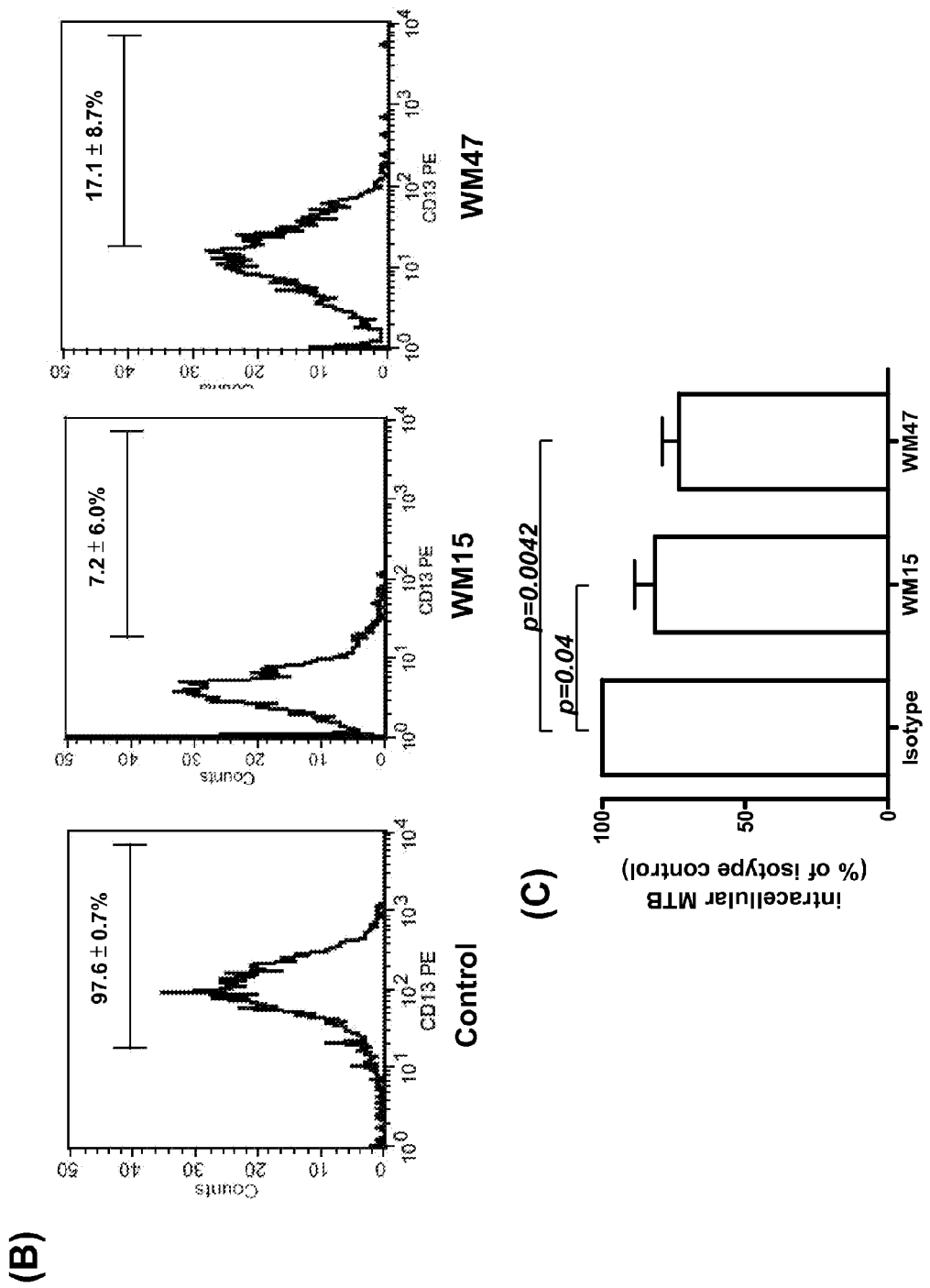

To understand if CD13 protein on the monocyte was related to the internalization of *Mycobacterium tuberculosis*, methods as described above was performed and results are shown in FIGS. 2B-2C. As shown in FIG. 2B, monocyte was first treated with two anti-CD13 antibodies, WM15 and WM47. Both antibodies reduced the expression level of CD13 protein, but their effects on aminopeptiase activity were different. WM15 strongly inhibited aminopeptidase activity of CD13 protein as reported in many publications, however, WM47 had no influence on aminopeptidase activity. Viable *Mycobacterium tuberculosis* and monocytes were treated with WM15 (10 μg/ml) or WM47 (10 μg/ml), and phycoeruthrin conjugated anti-CD13 antibody was added. Then flow cytometry was used for analysis. Comparing to the control group, CD13-positive ratio of the WM15 antibody treated group reduced from 97.6±0.7% to 7.2±6.0%, while the ratio of the WM47 antibody treated group decreased to 17.1-8.7%. The results indicated that these two antibodies could attenuate expression of CD13 protein successfully (FIG. 2 B).

To evaluate whether entry of *Mycobacterium tuberculosis* into monocytes was regulated by CD13 protein, monocytes were pre-treated with WM15 antibody and WM47 antibody, followed by incubation with *Mycobacterium tuberculosis* for 24 hrs. Our results showed that the ratio of *M. tuberculosis*-positive monocytes was significantly reduced by the treatment of 10 μg/ml WM15 (81.6±7.1%, P=0.04) or 1 μg/ml WM47 (73.2±6.0%, P=0.0042) as compared with that of isotype control (FIG. 2C).

EXAMPLE 3

Figure 3:
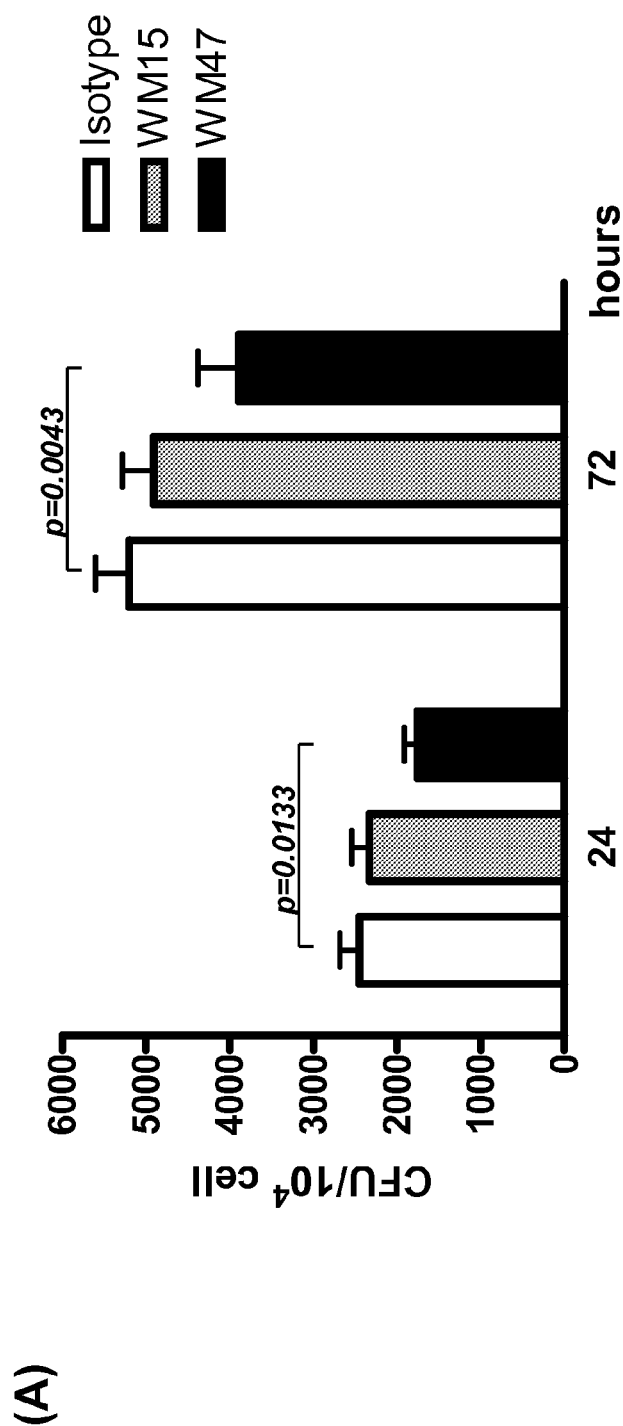
FIGS. 3A-3C demonstrate survival of *Mycobacterium tuberculosis* in monocytes. (A) Monocytes pretreated with corresponding isotype or WM15 or WM47 for 1 hour were incubated with *Mycobacterium tuberculosis* for 24 hours and 72 hours and then lysed. The lysates were cultured for *Mycobacterium tuberculosis* on 7H11 agar for 3 weeks, after which CFU were counted. Data represented means (±SEM) of eleven independent experiments. (B) Monocytes were infected with same amount of *Mycobacterium tuberculosis* for 1 hour, and then posttreated with corresponding isotype or WM15 or WM47 for 24 hours. CFU data represented means (±SEM) of thirteen independent experiments. (C) ROS generation of monocytes with or without *Mycobacterium tuberculosis* infection for 24 hours was measured by flow cytometry. Data were expressed as mean fluorescence intensity of DCFDA relative to control values (100%, isotype antibody) and three independent experiments were shown.
Figure 3:
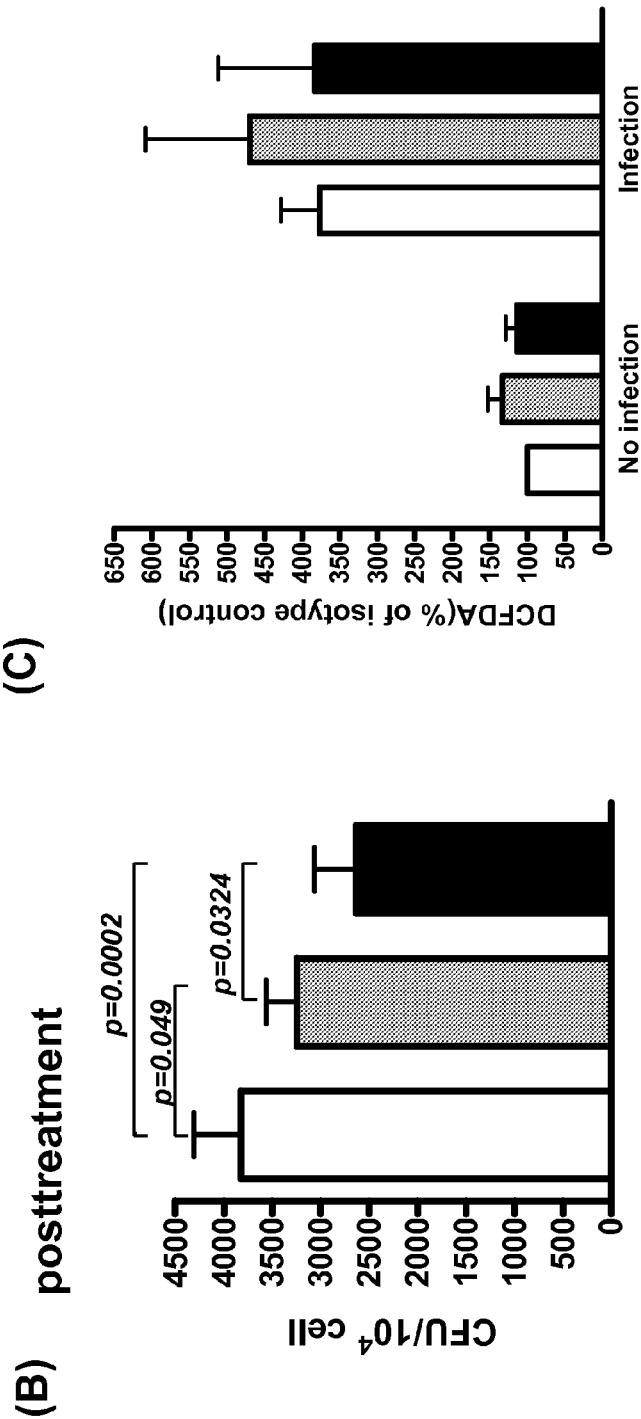

Role of CD13 Protein in Survival of *Mycobacterium tuberculosis* in Monocytes To further investigate the effects of CD13 on intracellular mycobacterial growth, *Mycobacterium tuberculosis* was cultured for 3 weeks from lysates of monocytes incubated with *Mycobacterium tuberculosis* for 24 and 72 hours. Colony Forming Unit (CFU) per 10,000 monocytes in WM15-treated cells was not different from cells pretreated with isotype control both in 24 hours and 72 hours groups (FIG. 3A). Whereas cells pretreated with WM47 produced significantly fewer CFU than isotype-treated controls infected for 24 hours (P=0.0133) and 72 hours (P=0.0043) (FIG. 3A). Thus, although WM15 and WM47 antibodies can both inhibit the entry of *Mycobacterium tuberculosis*, significantly fewer organisms actually survived inside cells treated with WM47.

To further identify effect of survival inhibition of WM15 antibody and WM47 antibody on *Mycobacterium tuberculosis* was not due to the effect in blocking bacterial entry, monocytes were infected with same amount of *Mycobacterium tuberculosis* for 1 hour, and then post-treated with either WM15 or WM47 for 24 hours. After 3 weeks of culture, the CFU count with WM47 (2635±430, P=0.0002) treatment as well as WM15 (3248±322, P=0.049) were significantly lower than that with isotype control (3587±594). Our data indeed showed that WM47 was superior in intracellular bacterial suppression than WM15 (FIG. 3B).

The results shown in FIG. 3B demonstrated that WM47 antibody had stronger inhibition on intracellular *Mycobacterium tuberculosis* than WM15 antibody (referring to FIGS. 3A-3B). In summary, these results demonstrated that CD13 could facilitate internalization of *Mycobacterium tuberculosis* into monocytes and inhibit survival of *Mycobacterium tuberculosis* in monocytes. When the signal transduction amplified by antibodies (especially WM47 antibody), *Mycobacterium tuberculosis* could not survive.

EXAMPLE 4

The Effect of CD13 on Microbicidal Capacity of Monocytes

Firstly, we assessed the ROS generation and cytokine production in monocytes infected with *Mycobacterium tuberculosis*. There was no significant difference in ROS production between isotype controls and in antiCD13 antibody-treated monocytes (FIG. 3C). Only slightly increase in TNF-alpha production was seen in WM15-treated and WM47-treated cells infected for 72 hrs (Table 1, paired T test).

To evaluate whether binding of CD 13 protein and WM15 antibody/WM47 antibody to *Mycobacterium tuberculosis* was related to phagosome formation during *Mycobacterium tuberculosis* infection, expression of Rab in monocytes was determined with or without CD13 antibody treatment. The method and process were the same as described above. Because Rab5 and Rab7 were known to be involved in regulation of phagosome maturation, Rab5 and Rab7 was main target of the study.

Figure 4:
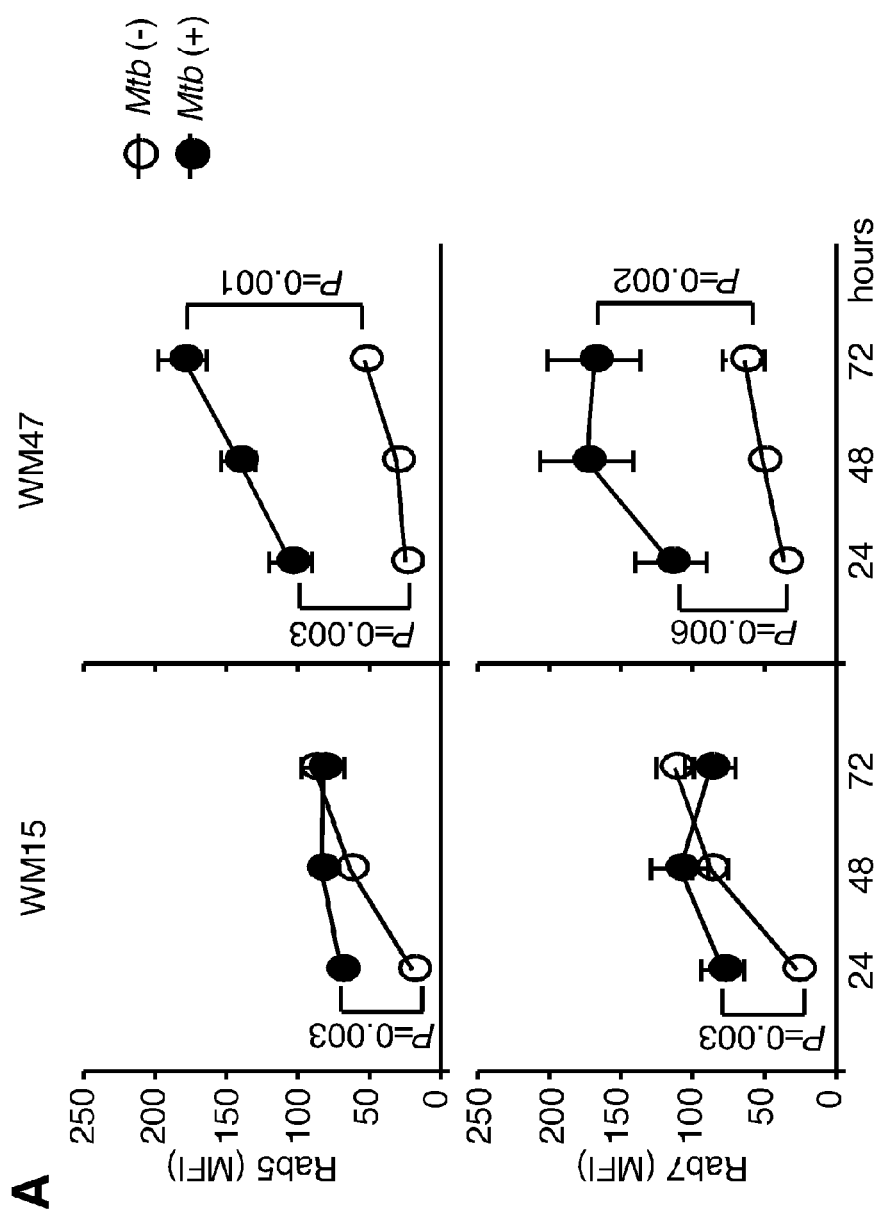
FIGS. 4A-4B show the effect of CD13 on microbicidal capacity of monocytes. (A) Monocytes were treated with WM15 antibody and WM47 antibody, with or without *Mycobacterium tuberculosis* infection for 72 hrs. Then intracellular Rab5 expression of monocytes was quantified. In the infection treated group, monocytes treated with WM47 antibody had highest Rab5 expression in 72 hrs (no infection vs. MTB infection, P=0.001), suggesting that binding of CD13 protein and WM47 antibody induced signal transduction to enhance Rab5 expression in infected monocytes. Also, infected cells treated with WM47 antibody showed significantly higher expression of Rab7 as compared with un-infected cells in 72 hrs (P=0.002). Data were expressed as mean fluorescence intensity of Rab5 or Rab7 and represented as means (±SEM) of seven independent experiments. (B) Endocytic pH was indicated by LysoSensor Yellow/Blue Dextran dye and the dual emission was measured at 420 nm (top panel) and 520 nm (bottom panel). The panels were representative images of *Mycobacterium tuberculosis* infected monocytes that treated with isotype, antiCD13 antibody WM15 or WM47, respectively. The 520/420 nm fluorescence ratio was calculated and the mean pH value was obtained by comparing with known pH standards (right top panel). The number of vesicles with pH<4.8 (active lysosomes) was counted and the percentage of active lysosomes was represented of nine independent experiments (right bottom panel).
Figure 4:
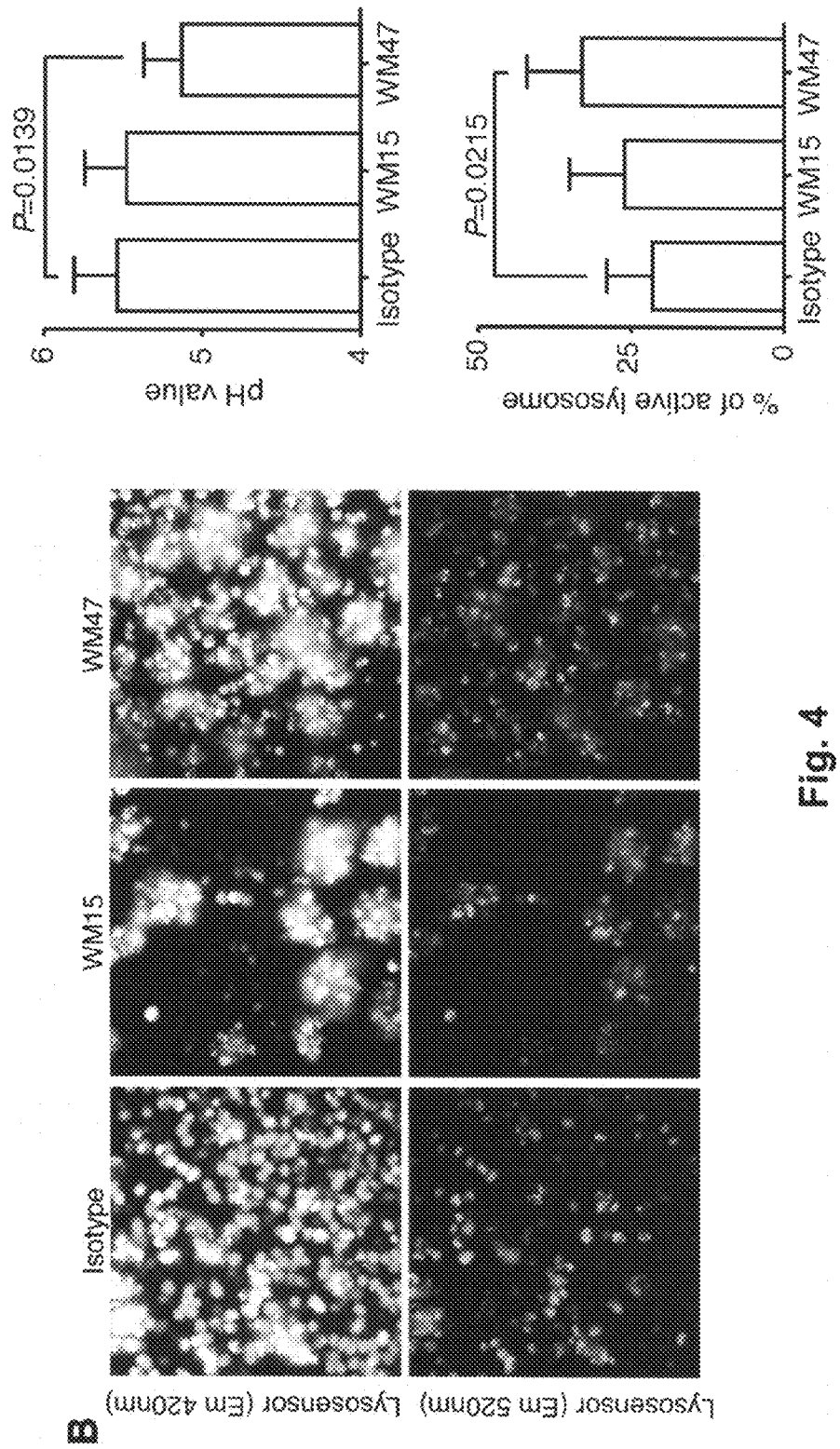

Rab5 and Rab7 expression were measured every 24 hours in monocytes pretreated with WM15 and WM47 and then incubated with *Mycobacterium tuberculosis* for 72 hours. Our data showed that treatment with WM47 induced a steady increase in Rab5 expression and a significant difference was found between infected and un-infection cells (FIG. 4A). The results were similar in the global expression of Rab7 between infected-cells and uninfected cells with the treatment of WM47 (FIG. 4A).

To understand whether the global increase in Rab expression was associated with phagosome maturation, we then studied phagosomal acidification by using a pH-sensitive dye, Lyso-Sensor Yellow/Blue. After 16 hours treatment, the average pH value of isotype, WM15 and WM47 treatment were 5.54±0.27, 5.48±0.26 and 5.13±0.24, respectively (FIG. 4B). The pH value of vesicles of WM47-treated monocytes was significantly lower than that of isotype-treated cell (P=0.0139). Since the pH value was associated with the stage of phagosomal maturation, the numbers of active lysosomes and inactive lysosomes identified by pH value were counted. Higher counts of active lysosomes (33.1±9.1%) were found in *Mycobacterium tuberculosis*-infected monocytes with WM47 treatment as compared to isotype (21.6±7.5%) and WM15 treatment (26.1±9.0%). The data inferred that WM47 treatment may promote the process of phagosome maturation in term of phagosomal acidification.

Take together, those data suggested that WM47 treatment could promote the process of phagosome maturation and control the survival of intracellular *Mycobacterium tuberculosis*.

EXAMPLE 5

The Effect of Cd13 on Cholesterol Uptake

Since lipid accumulation is tightly associated with the host response to *Mycobacterium tuberculosis* infection and the growth of intracellular *Mycobacterium tuberculosis*, we further investigated the effect of CD13 on cholesterol uptake of monocytes.

In isotype-treated monocytes, infection of *Mycobacterium tuberculosis* caused a marked intracellular accumulation of

TABLE 1

| Cytokine production as monocytes were infected with MTB for 24 and 72 hours | | | | | | |
|---|---|---|---|---|---|---|
| Cytokines | 24 hours | | | 72 hours | | |
| (pg/ml) | Isotype | WM15 | WM47 | Isotype | WM15 | WM47 |
| Pretreatment | | | | | | |
| TNF-alpha | 4757 ± 1354 | 5639 ± 993 | 5426 ± 955.2 | 4798 ± 2259 | 6434 ± 1529* | 5965 ± 1465* |
| IL-6 | 13729 ± 97 | 13754 ± 271 | 13462 ± 48 | 13195 ± 178 | 13506 ± 258 | 13169 ± 171 |
| Posttreatment | | | | | | |
| TNF-alpha | 6804 ± 1893 | 7223 ± 2190 | 6754 ± 2253 | 7120 ± 2925 | 8048 ± 3153 | 7343 ± 2909 |
| IL-6 | 11230 ± 106 | 11178 ± 83 | 10368 ± 183 | 9109 ± 618 | 9786 ± 128 | 9013 ± 141 |

Figure 5:
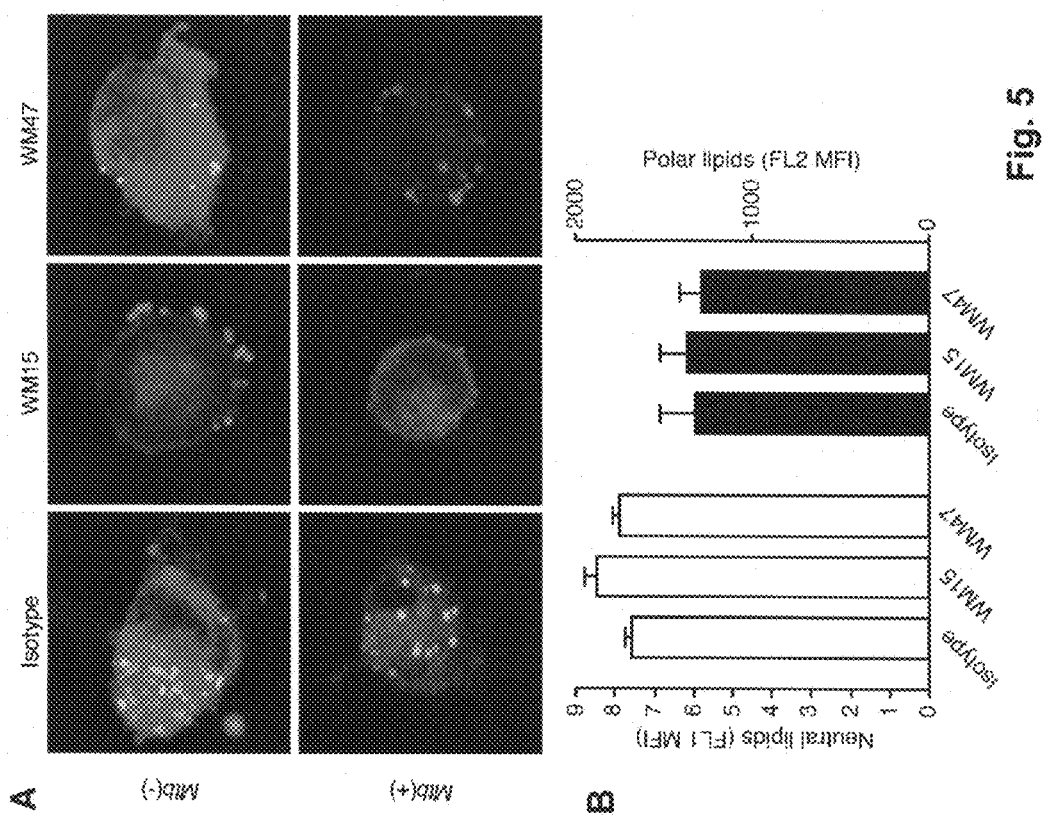
FIGS. 5A-5D show the effect of CD13 on cholesterol uptake. (A) Antibody-treated monocytes with or without *Mycobacterium tuberculosis* for 24 hours were stained by nile red and lipid associated nile red was viewed by cofocal microscopy (1000×) (yellow-gold fluorescence, excitation, 488 nm; emission, 529-560 nm and red fluorescence, excitation 543 nm; emission, 590-630 nm). (B) Nile red fluorescence was examined at two spectral settings, FL1 channel for neutral lipids and FL2 channel for polar lipids. The mean fluorescence intensity was quantified by flow cytometry. (C) BODIPY-labeled cholesterol (5 μg/ml) was added in the culture medium and the cholesterol uptake of monocytes with or without *Mycobacterium tuberculosis* infection was examined by flow cytometry. Data were expressed as percentages of cholesterol-BODIPY relative to control values (100%, isotype antibody) and five independent experiments were shown. (D) *M. tuberculosis* infected monocytes were treated with cholesterol (10 μg/ml) supplement plus isotype or WM15 or WM47 for 24 hours. CFU data represented means (±SEM) of six independent experiments
Figure 5:
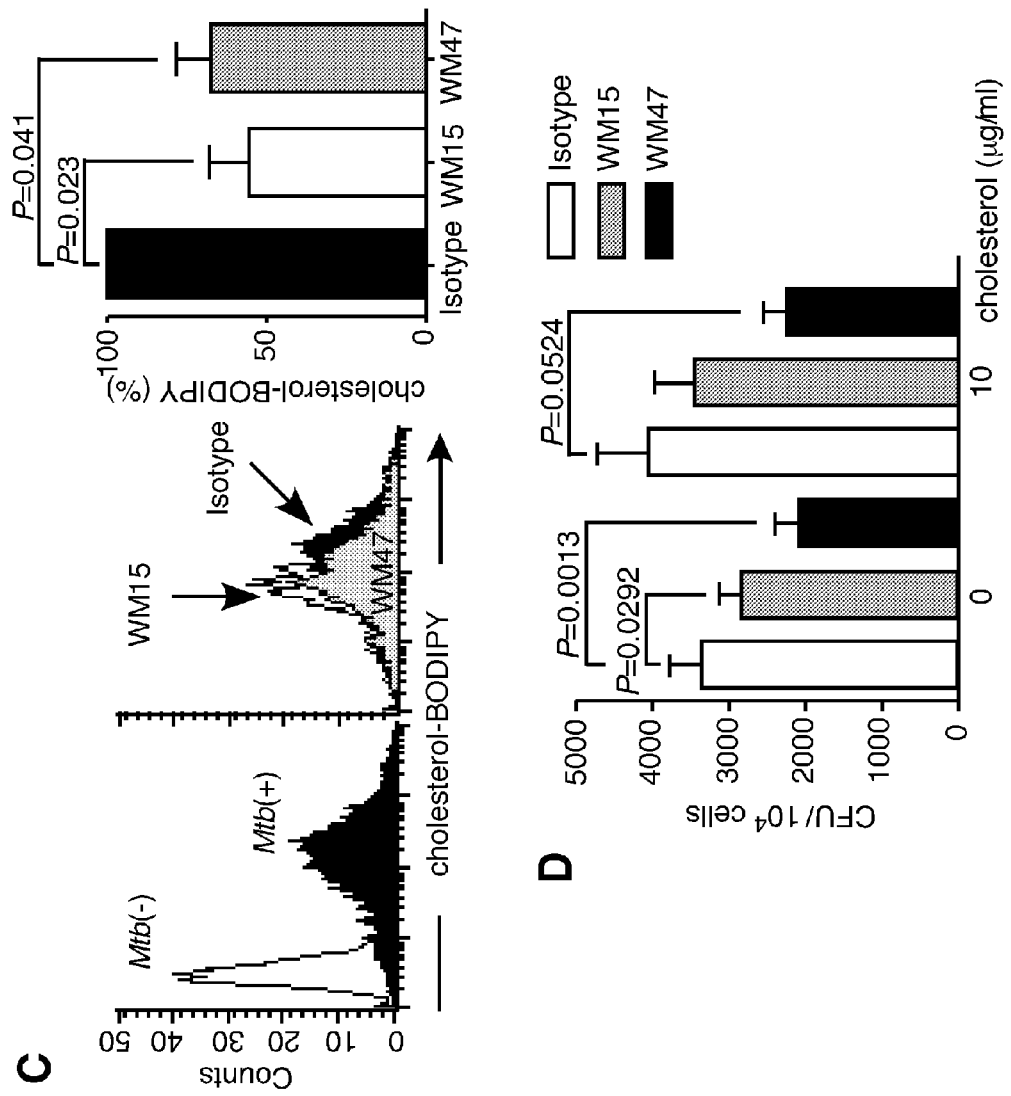

*Compared to Isotype control, P < 0.005 cholesterol, visualized by staining with nile red (FIG. 5A, left column). On the contrary, the internalization of cholesterol was significantly inhibited by the treatment of WM15 and WM47 compared to isotype controls, resulting in the accumulation of cholesterol around cell surfaces (FIG. 5A). The total lipid content was however not affected by the treatment of both CD13 antibodies (FIG. 5B).

To further confirm whether antiCD13 antibodies may inhibit the internalization of cholesterol, BODIPY labeled-cholesterol was added in the culture medium of antiCD13 antibody-treated cells for 24 hours. The results showed that monocytes infected with *Mycobacterium tuberculosis* allowed a substantial greater uptake of cholesterol into cells, whereas WM15 reduced the uptake to 55.35±12.5% and WM47 to 67.7±10.86% of isotype controls (FIG. 5C).

These data suggested that CD13 antibody could inhibit the internalization of cholesterol into monocytes infected with *Mycobacterium tuberculosis*.

We also estimated the contribution of CD13-mediated cholesterol transport to the intracellular survival of *M. tuberculosis*. *M. tuberculosis* infected monocytes were treated with or without cholesterol (10 µg/ml) supplement plus isotype or WM15 or WM47 for 24 hours. Then the lysates of monocytes were cultured for three weeks. Without the supply of cholesterol, the CFU counts of *M. tuberculosis* with WM47 (2084±313, P=0.0013) and WM15 (2833±301, P=0.0292) treatments were significantly less than that with isotype control (3353±439) (FIG. 5D). By giving 10 µg/ml cholesterol, the intracellular mycobacterial growth in WM15 treatment (3443±541) became no significant difference from that of isotype control (4055±669). However, WM47 treatment still showed its partial inhibitory effect upon mycobacterial growth (2259±286, P=0.0524).

These results indicate that dissimilar anti-CD13 antibodies might have different degrees of inhibition upon mycobacterial growth through its interference with cholesterol utilization.

CONCLUSIONS

The embodiments of the present invention used recombinant soluble CD13 protein, nano-particle bound CD13 protein, and membrane bound CD13 protein to demonstrate that soluble CD13 protein and membrane bound CD13 protein could bind to viable *Mycobacterium tuberculosis*, suggesting that CD13 protein of monocytes was a novel receptor to *Mycobacterium tuberculosis*. However, internalization of *M. tuberculosis* is apparently not dependent on the enzymatic activity of CD13, even though this activity is considered an essential biological function of the receptor. We demonstrated both anti-CD13 antibodies (WM15 and WM47) reduced the entry of the organism into monocytes by about 20% compared with cells treated with isotype antibody. However, WM15 inhibits CD13 enzymatic activity, whereas WM47 does not. Similar results have been reported for in vitro experiments with a human coronavirus and cytomegalovirus infection, showing that CD13-mediated uptake of virus was not dependent on its enzymatic activity. We also observed that soluble CD13-MNP bound nearly half the *M. tuberculosis* organisms in solution, but treatment of monocytes with anti-CD13 antibodies led to only a 20% reduction in *M. tuberculosis* internalization in cells. This supports the contention that *M. tuberculosis* enters monocytes via multiple receptors In fact, previous publications had shown that several ligands were expressed on the surface of *Mycobacterium tuberculosis*, which could interact with multiple receptors of phagocyte, including complement receptor 3 (CR3), mannose receptor (MR), surfactant proteins-A (SP-A), class A scavenger receptors (SR-A), and dendritic cell-specific ICAM-3 grabbing non-integrin, (DC-SIGN). Many receptors of phagocytes were lipid raft-associated and played a major or assistant role during binding, phagocytosis, movement and intracellular survival of *Mycobacterium tuberculosis*. Therefore, these receptors were related to phagocytosis process and influenced survival of intracellular *Mycobacterium tuberculosis*. For example, CR3 mediated phagocytosis had shown lack of and use of inflammation reaction caused by invasion of *Mycobacterium leprae* into phagocytes and mannose receptor (MR) internalization. CR3 might provide a mechanism for *Mycobacterium tuberculosis* to enter into phagocytes without triggering cell activation. It is believed that *Mycobacterium tuberculosis* used CR3 and MR as major receptors to attain survival in phagocytes. However, supplementation of inhibitors of these receptors such as anti-CR3 and anti-MR antibody, survival and growth of *Mycobacterium tuberculosis* in human phagocytes were changed. Our data indicated a somewhat different effect, in that treatment with 2 different CD13 antibodies affected both the internalization as well as intracellular survival of *Mycobacterium tuberculosis* in monocytes, particularly by a WM47 antibody. This implies that MW47-specific epitope on CD13 may be responsible to the negative impact on intracellular *Mycobacterium tuberculosis* survival through undefined mechanisms. It has been shown that crosslinking CD13 with a defined clone of CD13 antibodies could induce cell activation, including mitogen-activated protein kinase phosphorylation, calcium fluxing and homotypic aggregation of monocytes in an epitope-dependent way. Anti-CD13 antibody WM15 evokes a more sustained elevation of intracellular $Ca^{2+}$ in comparison with other clones and induces homotypic aggregation of monocytes at a low dose without inhibiting enzymatic activity. By contrast, anti-CD13 antibody WM47 doesn't induce homotypic aggregation. These findings suggested that CD13 may provoke a series of interactions to inhibit *Mycobacterium tuberculosis* intracellular survival. We found that either pre-treatment or post-treatment of monocytes with anti-CD13 antibody WM47 led to a more significant reduction in intracellular survival of *Mycobacterium tuberculosis* as compared to isotype-treated cells or those treated with WM15. Therefore, CD13-associated intracellular growth inhibition of *Mycobacterium tuberculosis* may be epitope-dependent.

In the following studies we sought to identify the mechanisms underlying the differential effects on bacterial intracellular survival by WM15 and WM47. Since *Mycobacterium tuberculosis* escapes from phagosomes and grows within the cytosol of phagocytes mainly by modulating the phagosome-associated Rab network, global expressions of Rab5 and Rab7 in monocytes were firstly investigated. We found that pretreatment of healthy monocytes with WM15 or WM47 anti-CD13 antibodies resulted in up-regulation of Rab5 and Rab7 when the cells were subsequently infected with *Mycobacterium tuberculosis*. Interestingly however, only WM47 antibodies caused a sustained and significantly increase of both Rab5 and Rab7 protein levels. We found that pretreatment of healthy monocytes with WM15 or WM47 anti-CD13 antibodies both resulted in global up-regulation of Rab5 and Rab7, when the cells were subsequently infected with *Mycobacterium tuberculosis*. This suggests that a WM47-dependent CD13 pathway may reverse the phagosome maturation arrest induced by *Mycobacterium tuberculosis*. In addition, our data also showed that the mean pH was significantly lower and the numbers of active lysosomes with a pH less than 4.8 was significantly higher in cells treated with WM47 but not in isotype control and WM15. It appears that distinct receptor-mediated pathways may dictate the intracellular trafficking of *Mycobacterium tuberculosis*-associated phagosomes, so it is reasonable to speculate that internalization of *Mycobacterium tuberculosis* through CD13 may also affect such pathogen-associated phagosomes through CD13-mediated signaling. Although phagosomal acidification is an important feature indicating the activation of effector functions by host cells, the effect of phagosomal acidification per se as a major bactericidal factor against *Mycobacterium tuberculosis* is however difficult to determine. In summary, our results support the reversal by WM47 of *Mycobacterium tuberculosis*-associated arrest of phagosome maturation as well as CD13 epitope-dependent inhibition of intracellular *Mycobacterium tuberculosis* growth. Of course, maturation of the phagosome is a dynamic process, and our study was only able to take snapshots of this process at certain static points. However, our findings do add to the understanding of the complex relationships between mycobacteria and the phagocytes they infect.

*Mycobacterium tuberculosis* utilizes cholesterol in a variety of ways to invade and survive in the cells. It has been demonstrated that *Mycobacterium tuberculosis*, by entering host cells at cholesterol-rich domains of plasma membrane, may ensure their subsequent survival within phagosomes. Once inside the macrophages, *Mycobacterium tuberculosis* may transform to a dormant non-replicating state and induce the formation of lipid-laden foamy macrophages. *Mycobacterium tuberculosis* adapts to survive in the nutrition-restrictive macrophages mainly by switching metabolic requirement to utilize cholesterol as a major source of energy. It has been shown that host genes encoding enzymes involved in lipid metabolism were up-regulated within human pulmonary tuberculomas. Our proteomic data derived from in-vitro stimulation of monocytes by heat-killed *Mycobacterium tuberculosis* also supported these findings that up-regulation of proteins involved in lipid metabolism can be one of the major host responses to *Mycobacterium tuberculosis*. Nevertheless, the finding that anti-CD13 antibodies blocked cellular cholesterol uptake by monocytes was unexpected. The association of cholesterol absorption and CD13 was first and only described by identifying this 145 kDa enterocyte integral membrane protein as a molecular target for cholesterol absorption inhibitor Ezetimibe. The mechanisms by which CD13 mediates cholesterol transport into cells was however not clear. Several consensus amino acid sequences have been suggested to have high binding affinity to cholesterol, namely cholesterol recognition/interaction amino acid consensus (CRAC) motif and cholesterol consensus motif (CCM). These cholesterol binding motifs can be located adjacent to the trans-membrane region of CD13, including 4 CRAC (30VVYSQEK36, 88LRPYLTPNDR97, 155VEPTEYLVVHLK166 and 283VSEFDYVEK291) and 3 CCM (152KTELVEPTEYLVVHL166, 710RSEVYGPMKNYLKKQV725 and 835KELWILNRYLSYTL848). Despite the existence of these structural motifs in CD13 sequence, the role of these motifs in the machinery operating cholesterol transport by CD13 remains to be elucidated. Finally, the growth inhibition by anti-CD13 antibodies could be reversed by the supplementation of excess cholesterol suggesting that CD 13-mediating cholesterol uptake indeed plays a significantly role in the intracellular survival of *Mycobacterium tuberculosis*.

In summary, the present invention provided embodiments that demonstrated CD13 protein of monocytes was a novel receptor to *Mycobacterium tuberculosis*. CD13 protein could facilitate entry of *Mycobacterium tuberculosis* into human monocytes and inhibit survival of *Mycobacterium tuberculosis* in monocytes.

What is claimed is:

1. A method for reducing survival of *Mycobacterium tuberculosis* in a cell, comprising: administering an effective amount of a WM47 antibody to the cell, wherein the WM47 antibody protects the cell against *Mycobacterium tuberculosis* by binding a CD13 receptor of the cell.

2. The method according to claim 1, wherein the WM47 antibody reduces an expression level of the CD13 receptor.

3. The method according to claim 1, wherein the WM47 antibody reduces endocytic internalization of *Mycobacterium tuberculosis* entering into the cell.

4. The method according to claim 1, wherein the WM47 antibody is used in pre-treatment of the cell.

5. The method according to claim 1, wherein the WM47 antibody is used after *Mycobacterium tuberculosis* infection of the cell.

6. The method according to claim 1, wherein the cell is a human monocyte.

* * * * *

SEQUENCE LISTING

<160> NUMBER OF SEQ ID NOS: 7

<210> SEQ ID NO 1
<211> LENGTH: 7
<212> TYPE: PRT
<213> ORGANISM: Artificial Sequence
<220> FEATURE:
<223> OTHER INFORMATION: cholesterol recognition/interaction amino acid
      consensus (CRAC) motif

<400> SEQUENCE: 1

Val Val Tyr Ser Glx Glu Lys
1               5

<210> SEQ ID NO 2
<211> LENGTH: 10
<212> TYPE: PRT
<213> ORGANISM: Artificial Sequence
<220> FEATURE:
<223> OTHER INFORMATION: cholesterol recognition/interaction amino acid
      consensus (CRAC) motif

<400> SEQUENCE: 2

Leu Arg Pro Tyr Leu Thr Pro Asn Asp Arg
1               5                   10

<210> SEQ ID NO 3
<211> LENGTH: 12
<212> TYPE: PRT

```
<213> ORGANISM: Artificial Sequence
<220> FEATURE:
<223> OTHER INFORMATION: cholesterol recognition/interaction amino acid
      consensus (CRAC) motif

<400> SEQUENCE: 3

Val Glu Pro Thr Glu Tyr Leu Val Val His Leu Lys
1               5                   10

<210> SEQ ID NO 4
<211> LENGTH: 9
<212> TYPE: PRT
<213> ORGANISM: Artificial Sequence
<220> FEATURE:
<223> OTHER INFORMATION: cholesterol recognition/interaction amino acid
      consensus (CRAC) motif

<400> SEQUENCE: 4

Val Ser Glu Phe Asp Tyr Val Glu Lys
1               5

<210> SEQ ID NO 5
<211> LENGTH: 15
<212> TYPE: PRT
<213> ORGANISM: Artificial Sequence
<220> FEATURE:
<223> OTHER INFORMATION: cholesterol consensus motif (CCM)

<400> SEQUENCE: 5

Lys Thr Glu Leu Val Glu Pro Thr Glu Tyr Leu Val Val His Leu
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: cholesterol consensus motif (CCM)

<400> SEQUENCE: 6

Arg Ser Glu Val Tyr Gly Pro Met Lys Asn Tyr Leu Lys Lys Gln Val
1               5                   10                  15

<210> SEQ ID NO 7
<211> LENGTH: 14
<212> TYPE: PRT
<213> ORGANISM: Artificial Sequence
<220> FEATURE:
<223> OTHER INFORMATION: cholesterol consensus motif (CCM)

<400> SEQUENCE: 7

Lys Glu Leu Trp Ile Leu Asn Arg Tyr Leu Ser Tyr Thr Leu
1               5                   10
```